United States Patent [19]

Cooke et al.

[11] Patent Number: 5,635,366
[45] Date of Patent: Jun. 3, 1997

[54] PREDICTIVE ASSAY FOR THE OUTCOME OF IVF

[75] Inventors: Brian Cooke; Anthony Michael, both of London, United Kingdom

[73] Assignee: Royal Free Hospital School of Medicine, United Kingdom

[21] Appl. No.: 522,410

[22] PCT Filed: Mar. 23, 1994

[86] PCT No.: PCT/GB94/00596

§ 371 Date: Sep. 21, 1995

§ 102(e) Date: Sep. 21, 1995

[87] PCT Pub. No.: WO94/21815

PCT Pub. Date: Sep. 29, 1994

[30] Foreign Application Priority Data

Mar. 23, 1993 [GB] United Kingdom .................. 9305984

[51] Int. Cl.$^6$ .................................................... C12Q 1/32
[52] U.S. Cl. .............................. 435/26; 435/806; 436/817
[58] Field of Search ................................... 435/4, 26, 31, 435/806; 436/817

[56] References Cited

U.S. PATENT DOCUMENTS 4,815,835  3/1989  Corona ................................. 350/507
5,173,404  12/1992  DiZerega .............................. 435/7.1

OTHER PUBLICATIONS

Fateh, M., Cortisol Levels in Human Follicular Fluid, Fertility and Sterility 51(3) 538–541. Mar. 1989.
McAllister, J., Proliferating Human Granulosa Lutein Cells in Long Term Monolayer Culture: Expression of Aromatase, Cholesterol Side–Chain Cleavage, and 3betaHydroxysteroid Dehydrogenase, J of Clinical Endo and Metabolism, 71(1) 26–33.1990.
Benediktsson, R., 11betaHydroxysteroid Dehydrogenase in the Rat Ovary: High Expression in the Oocyte, J of Endocrinology 135 53–58. 1992.
The Lancet, vol. 342, No. 8873, Sep. 18, 1993, pp. 711–712. Michael et al, 'Ovarian 11Betahydroxysteroid dehydrogenase: potential predictor of conception by in–vitro fertilisation and embryo transfer'.
Journal of Endocrinology, vol. 135, 1992 pp. 53–58, Benediktsson et al. '11ss–Hydroxysteroid dehydrogenase in the rat ovary: high expression in the oocyte'.
The Journal of Clinical Endocrinology & Metabolism vol. 71 No. 5, Nov. 1990, pp. 1375–1376, Anderson 'Levels of Steroid–Binding Proteins and Steroids in Human Preovulatory Follicle et al.'.
Fertility and Sterility vol. 51 No. 3, Mar. 1989 pp. 538–541, Fateh et al, 'Cortisol levels in human follicular fluid'.
Clinical Endocrinology, vol. 38, 3 Jun. 1993, pp. 641–644, Michael et al, 'Direct inhibition of ovarian steroidogenesis by cortisol and the modulatory role of 11Beta–hydroxysteroid dehydrogenase'.

*Primary Examiner*—Ralph Gitomer
*Attorney, Agent, or Firm*—Nixon & Vanderhye

[57] ABSTRACT

The present invention provides a method for predicting the outcome of IVF which comprises:

(i) determining the level of 11β-hydroxysteroid dehydrogenase (11β-HSD) in a biological sample from a female patient; and (ii) predicting from the level of 11β-HSD determined the probability of establishing pregnancy in said subject by IVF.

It has been found that there is an inverse correlation between the levels of 11β-HSD in the environment of the oocyte and subsequent establishment of pregnancy by IVF. The present invention also provides methods of screening female subjects for their suitability to take part in IVF programs, and kits to use in determining levels of 11β-HSD.

17 Claims, 1 Drawing Sheet

PREDICTIVE ASSAY FOR THE OUTCOME OF IVF

The present invention relates to an assay which is predictive of the outcome of in vitro fertilisation (IVF) in mammals including humans.

BACKGROUND OF THE INVENTION

The technique of IVF has been used in human patients with infertility problems successfully since 1978. Despite extensive research it is still a difficult procedure and even in the best IVF clinics a success rate of only 30% is generally achieved.

IVF is an expensive procedure and can also be psychologically traumatic for a patient. Surgical procedures are required to collect eggs for IVF and following fertilization, further surgery is required to implant fertilised eggs in the womb. The recipient must then wait for a period of time before it can be determined whether or not pregnancy has been established. In some cases, pregnancy may never be established despite repeated attempts and these cases represent a considerable expense to society, both in financial and human terms.

Therefore, until success rates of IVF can be improved, it would be desirable to be able to identify recipients for whom IVF is unlikely to be successful prior to treatment, so that such patients avoid the abovementioned costs of the IVF procedure.

The adrenal steroid hormone, cortisol, is believed to influence maturation of the female germ cell (the oocyte) and the development of ovarian cells in culture (Orly & Sato (1979) Cell 17,295; Patino & Thomas, (1990) J. Exp. 2006 255,97). Recently, Fateh et al (1989, Fertil. Steril. 51,538–541) have reported that there is an association between the concentration of cortisol in follicular fluid and oocyte maturity.

The enzyme 11β-hydroxysteroid dehydrogenase (EC 1.1.1.146) converts cortisol to its inactive form, cortisone. Benediktsson et al (J. Endocrinology (1992) 135, 53–58) report the presence of 11β-hydroxysteroid dehydrogenase (11β-HSD) in rat oocytes. The results of Benediktsson et al suggest a role for 11β-HSD in modulating ovarian function. Two isoforms of 11β-HSD have been characterised; a hepatic form and a renal form. Our initial findings suggest that both isoforms are expressed in ovarian tissue. In the present invention, reference to 11β-HSD includes both isoforms.

DESCRIPTION OF THE INVENTION

Studies such as those mentioned above have tended to focus upon the relationship between oocyte maturity or hormone levels and the success of fertilization in vitro. However, we have surprisingly found that once fertilisation has been achieved and the second part of the IVF procedure is performed, namely implantation, there is a strong inverse correlation between levels of 11β-HSD in the environment of the oocyte at the time of collection and the subsequent establishment of pregnancy. This correlation exists regardless of the maturity of the oocyte or other factors which may affect fertilization.

The present invention thus relates to assay methods and assay kits which can be used to predict the outcome of IVF in a female patient. The invention also relates to such methods and kits for use in a method of diagnosis in order to determine the outcome of IVF or the suitability of a female patient for IVF treatment. Although our invention described below has been developed from research on human female patients, it will be applicable to any mammalian female and can be used to increase the success of, for example, captive breeding programs of endangered species or commercial breeding by IVF of livestock such as cattle or horses.

Thus in one aspect the invention comprises a method for predicting the outcome of IVF which comprises:

(i) determining the level of 11β-hydroxysteroid dehydrogenase (11β-HSD) in a biological sample from a female subject; and (ii) predicting from level of 11β-HSD determined the probability of establishing pregnancy in said subject by IVF.

With regard to step (i), the sample may be a body fluid or a tissue such as the tissue from the environment of the oocyte such as the granulosa-lutein cells or follicular cells recovered for example from the ovarian follicles of women undergoing oocyte recovery for in vitro fertilization and embryo transfer. Alternatively the sample may be follicular aspirates, for example obtained on an out-patient basis prior to admission to an IVF program. The sample may also comprise stored (usually frozen) cells from the environment of an oocyte. Other samples include urine, follicular fluid and plasma.

Figure 1:
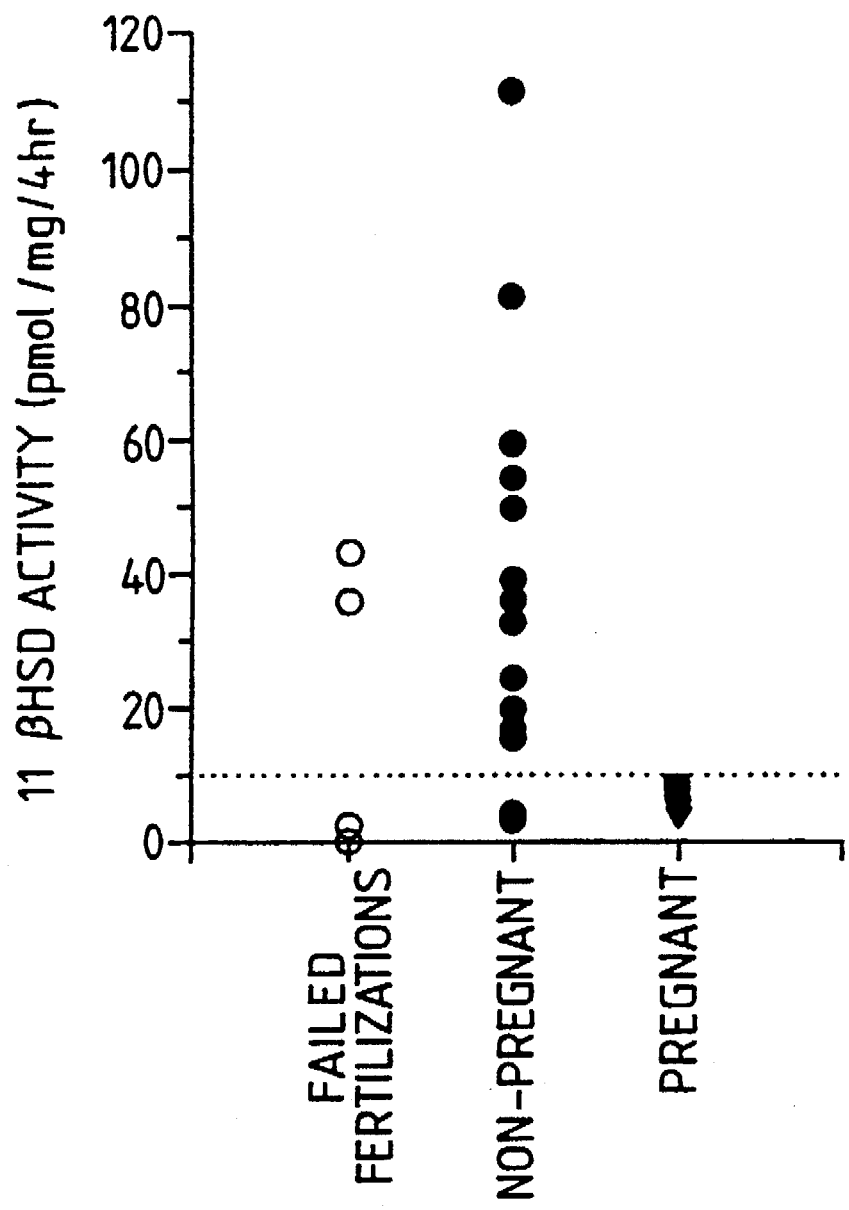
FIG. 1 shows the relationship of ovarian 11β-HSD activity to the outcome of IVF-embryo transfer (IVF-ET). "Failed fertilisations" =total failure of any recovered oocytes to fertilize. "Non-pregnant" =patients with oocytes that fertilized but that did not become pregnant after embryo transfer.

The level of 11β-HSD can be determined directly or indirectly. For the purposes of the invention the level of 11β-HSD may be measured as an amount or in terms of activity. Direct methods include enzyme assays to determine the level of 11β-HSD activity which involve supplying a substrate to the sample, for example $^3$H-cortisol, and measuring the conversion of the substrate (eg. to $^3$H-cortisone) by the enzyme. $^3$H-Cortisol and $^3$H-cortisone can be separated by thin layer chromatography and then quantified. This will provide a direct measurement of enzyme activity, and for this reason is preferred. In a typical assay, a concentration of about 100 nM of $^3$H-cortisol may be used, although anywhere from 10nM to 1000 nM or more can be used.

Indirect methods of measuring 11B-HSD include measuring the levels of cortisol and cortisone in the sample, and determining the ratio of the two as an indirect measure of enzyme activity. In such a case, the higher the level of cortisone in relation to cortisol, the higher the activity of the enzyme. The levels of cortisol and cortisone can be measured by methods known per se (eg by immunoassay methods having resolved cortisol and cortisone by TLC/MPLC). Commercially available kits for the assay of cortisol are available (see for example Kirk-Othmer Encyclopedia of Chemical Technology, 1982, Vol. 19, pages 631–632).

Alternatively, the 11B-HSD could be measured by immunoassay or similar ligand-binding techniques. This will provide an indication of the amount of the enzyme, which may be correlated to the enzyme activity. For example, a monoclonal antibody capable of binding the enzyme could be used in immunoassay methods such as RIA or ELISA. Methods to determine and obtain ligands which bind with high affinity to a specific analyte in are also available in the art; see for example WO89/09088 entitled "Paralog Affinity Chromatography".

The expression of the 11βHSD enzyme could also be measured by immunocytochemistry using a monoclonal antibody. Such techniques will provide a measurement of the amount of 11B-HSD present, which can be correlated to enzyme activity.

Although herein we refer to determining levels of 11β-HSD it will be understood from the foregoing that this includes the indirect measurements mentioned above.

Once the level of 11β-HSD has been measured, the result can be used to predict the likelihood of successful establishment of pregnancy in a female subject undergoing IVF treatment. In our studies, we have measured 11β-HSD levels as the amount of cortisol converted to cortisone per mg protein per 4 hours to obtain a direct measurement of enzyme activity. We have found that those subjects with enzyme activities less than about 10 pmol/mg/4 hr have a pregnancy rate of over 80% following embryo transfer. In contrast, subjects with enzyme activities that ranged from 15 to 111 pmol/mg/4 hr did not become pregnant even though fertilization of their oocytes was apparently successful.

Those of skill in the art will appreciate that although in our research we have determined a "cut-off" level of 11β-HSD activity above which patients have not become pregnant (and below which patients have significantly improved probability of successful pregnancy), the value is a statistical measure and other measurements and thresholds can be used. In practising the invention, it is most important to achieve consistency of assay, and so each individual practitioner (or IVF team) will be capable of establishing their own particular assay method and determining their own "cut-off" level. This could be established by first conducting a historical study on samples from previous patients.

Thus, the level of an enzyme activity of 10 pmol/mg/4 hr mentioned above represents the measure we have used in our studies as a suitable limit. However, if levels of 11β-HSD were to be measured in any of the other ways mentioned above, it would be desirable to conduct, using routine procedures, a control using our method of assay in order to determine the relationship between our results and the results of other methods, in order to make direct comparisons.

Once the level of 11β-HSD has been determined, it can be used to assess the likelihood of establishing pregnancy by IVF in a patient. For example, we have used our invention on samples from patients who have already had oocytes collected, fertilised in vitro, and implanted. Generally, a number of eggs are collected and fertilised so that in the event of failure to establish pregnancy, more fertilized eggs can be implanted. By conducting the method of the present invention, it is possible to predict, where pregnancy is not established, whether implantation of stored oocytes is likely to be successful. If levels of 11β-HSD in such patients is significantly above the level associated with successful pregnancy, then it would be a saving in time, money and stress to the patient not to undertake further attempts at implantation with stored oocytes collected and fertilized at the same time as those previously implanted and for which 11β-HSD data are available.

The present invention may also be performed prior to implantation, prior to fertilization of collected oocytes or even prior to collection of such oocytes. In such cases, it will be possible for the practitioner (or IVF clinic) to decide whether or not to even attempt a first implantation.

Thus, the present invention also provides a method for predicting the outcome of IVF in a female subject which comprises:

(i) removing a biological sample from the subject;

(ii) determining the level of 11β-hydroxysteroid dehydrogenase (11β-HSD) in said sample; and (iii) predicting from the level of 11β-HSD determined the probability of establishing pregnancy in said patient by IVF.

Suitable biological samples include those mentioned hereinbefore. This embodiment of the invention can be used to select likely candidates for an IVF program. Once a candidate has been selected, it will be desirable to confirm their suitability during the IVF procedure by repeating assays for 11β-HSD during the initial part of the IVF procedure.

Thus, the invention also comprises a method for establishing the likelihood of successful IVF treatment in a patient which comprises:

(i) removing oocytes from a female subject together with a biological sample;

(i') fertilising said oocytes in vitro;

(ii) determining the level of 11β-hydroxysteroid dehydrogenase (11β-HSD) in said sample; and (iii) predicting from the level of 11β-HSD determined the probability of establishing pregnancy in said subject by IVF.

Optionally, this embodiment of invention further comprises:

(iv) implanting into the female subject the fertilized oocytes.

Preferred biological samples include granulosa lutein cells.

In an alternative embodiment, the invention comprises:

(i) removing oocytes from a female subject together with a biological sample;

(ii) determining the level of 11β-hydroxysteroid dehydrogenase (11β-HSD);

(iii) predicting from the level of 11β-HSD determined the probability of establishing pregnancy in said subject by IVF; and (iii') fertilising oocytes from those subjects whose 11β-HSD level is below a predetermined threshold.

Optionally, this embodiment of invention further comprises (iv) implanting into the female subject the fertilized oocytes.

Preferred biological samples include granulosa lutein cells.

Although both the above embodiments are desirably practised on patients who have already been assayed prior to oocyte collection for suitable levels of 11β-HSD, they may also be practised on patients who have not undergone such an initial screen.

The invention finds application in large scale screening programs of potential IVF recipients who have been referred to, or present themselves at, IVF clinics. In this embodiment, the invention comprises:

(i) screening a population of female patients seeking treatment for infertility by IVF for levels of 11β-HSD; and (ii) selecting from the population those patients who have 11β-HSD levels below a predetermined threshold for IVF treatment. In particular, those patients who have 11β-HSD levels in the environment of the ovary, especially in granulosa lutein cells, below a predetermined threshold are preferred as suitable recipients for IVF treatment.

By use of the present invention, it will be possible for IVF clinics to allocate resources more efficiently, so that patients with high levels of 11β-HSD in the environment of a recovered oocyte who are unlikely to become pregnant by IVF treatment are not treated.

The levels of 11β-HSD in a female subject may be monitored over a period of time in order to establish whether or not changes favourable to successful IVF occur. We have found that the levels of ovarian 11β-HSD in individual patients does vary between consecutive menstrual cycles and therefore patients may be monitored in accordance with the invention to obtain an oocyte which is from an environment with favourable (i.e. low) levels of 11β- HSD.

Patients may also be treated to modulate or block 11β-HSD activity in vivo prior to oocyte recovery. For example, antibodies against 11β-HSD could be introduced into the patient in order to inhibit enzyme activity. This is analogous to methods of treating tumours or other conditions using antibody therapy. For the purposes of this invention, the term "antibody", unless specified to the contrary, includes fragments of whole antibodies which retain their binding activity for a tumour target antigen. Such fragments include Fv, F(ab') and F(ab')$_2$ fragments, as well as single chain antibodies. Furthermore, the antibodies and fragments thereof may be humanised antibodies, eg. as described in EP-A-239400 (Winter).

It may also be possible to inhibit the activity of 11β-HSD using other glucocorticoid hormones or analogues thereof which compete with cortisol for 11β-HSD. Such hormones or analogues thereof can be obtained by screening candidate hormones or analogues thereof by adding them to the assay described in Example 1 to see whether they can compete with $^3$H-cortisol for 11β-HSD, and thus inhibit the activity of the enzyme. Candidate hormones or analogues thereof may then be screened by administering an effective amount of a hormone or analogue thereof to female subjects undergoing IVF treatment who are found to have levels of 11β-HSD which are unfavourable to establishing pregnancy following IVF-ET. The amount of hormone or analogue thereof to be administered will need to be determined by the physician, taking into account the activity of the hormone and the condition of the patient. This can be achieved without difficulty, given that such hormones are often used in clinical practice in fertility clinics. The hormones or analogues thereof may be administered by any suitable route, e.g. orally or by injection. For administration, the hormone or analogue thereof may be formulated with a pharmaceutically acceptable carrier or diluent.

In such ways, it will be possible to modulate the levels of 11β-HSD activity in a patient desiring to undergo IVF so that the outcome of IVF will be successful.

Antibodies against 11β-HSD for use in the present invention may be monoclonal or polyclonal antibodies. Monoclonal antibodies may be prepared by conventional hybridoma technology using the proteins or peptide fragments thereof, as an immunogen. Polyclonal antibodies may also be prepared by conventional means which comprise inoculating a host animal, for example a rat or a rabbit, with a peptide of the invention and recovering immune serum.

The use of 11β-HSD inhibitors will also permit in vitro treatment of collected oocytes to reduce enzyme activity prior to fertilization of oocytes. This may be achieved by bringing into contact an effective amount of such an inhibitor, for example a hormone or analogue thereof as mentioned above, with a sample comprising an oocyte and surrounding tissue such as the granulosa lutein cells, in order to inhibit the activity of 11β-HSD in the sample. The sample and inhibitor may be brought into contact under sterile conditions such as those typically used for IVF.

The present invention also provides kits for use in performing the assay of the invention. Such kits include at least one reagent useful for the detection of 11β-HSD activity. Suitable reagents include antibodies, or other suitable ligand-binding reagents, against 11β-HSD optionally linked to a label. Typical labels are those commonly used in immunoassay procedures, for example horse radish peroxidase. Alternatively, the kit may contain antibodies, or other suitable ligand-binding reagents, against cortisol and/or cortisone. The kit may also contain standards, for examples predetermined amounts of cortisone, cortisol or 11β-HSD, any or all of which may be labelled with a detectable label. The kit may also contain enzyme cofactors, for example NAD or NADP which are converted to NADH or NADPH respectively.

The invention also provides a kit for the measurement of 11β-HSD for use in a method of diagnosis, prognosis, and/or IVF treatment of a female subject.

The invention also comprises the use of the abovementioned antibodies, fragments and variants thereof, and other suitable ligand-binding reagents, which may optionally be labelled with a detectable label for the manufacture of a diagnostic kit for use in the treatment or diagnosis of suitability for IVF.

Levels of 11β-HSD may also be assayed via analysis of the levels of 11β-HSD mRNA present in samples obtained. In order to achieve this, 11β-HSD cDNA (Tannin et al, (1991) J. Biol. Chem 266, 16653–16658) or fragments thereof may be used as a probe to determine levels of 11β-HSD in the environment of the oocyte. Such probes may also be formulated into kits in a manner analogous to those described for antibodies, and may contain control nucleic acids. Probes for the 11β-HSD gene may be designed for use as probes, for example for use in a nucleic acid amplification assay.

The following examples illustrate the invention.

EXAMPLE 1

Methods

Multiple follicular development was induced in IVF patients by the administration of busurelin and exogenous gonadotrophins. Follicles were aspirated transvaginally and the granulosa cells isolated from the follicular aspirates using a 60% (v/v) Percoll gradient. After washing with phosphate buffered saline, cells were suspended at a density of $5 \times 10^4$ cells/ml in mixed culture medium (1:1 Ham's F-12:DMEM) supplemented with 10% (v/v) foetal calf serum. Cells were then cultured for 3 days at 37° C. with daily replacement of medium. On the fourth day of culture 11βHSD activity was assayed by incubating the cells for 4 hours in serum-free medium containing 100 nM $^3$H-cortisol. At the end of the assay, steroids were extracted from the culture medium with chloroform, concentrated into ethyl acetate and separated by thin layer chromatography (TLC). Areas of cortisol and cortisone were visualized on the TLC plate by the absorption of ultraviolet light. They were then transferred to scintillation vials and the ratio of cortisone:cortisol determined by liquid scintillation counting. After correction for the specific activity of the $^3$H-cortisol and the concentration of cellular protein in each culture well, 11βHSD activities were expressed as the amount of cortisol converted to cortisone/mg protein/4 hours. The lower detection limit of the assay (represented on FIG. 1 by the horizontal dotted line) equated to 10 pmol/mg/4 hr.

Results

The distribution of 11βHSD activities, grouped by IVF-ET outcome, are presented in FIG. 1. Cells from 13 of the 29 patients in this study lacked detectable 11HSD activity. Of these 13 11βHSD negative patients, 2 (i.e. 15.4%) had no fertilization of any of the recovered oocytes while 9 of the remaining 11 patients became pregnant giving a pregnancy rate of 81.8% on embryo transfer. In contrast, 16 patients had detectable 11βHSD activities ranging from 15.61 to 111.25 pmol/mg/4 hr. Of these 16 11βHSD positive patients, 5 (i.e. 31.3%) had total fertilization failure (only two shown on FIG. 1) and none of the remaining 11 patients became pregnant on embryo transfer. While the rate of total fertilization failure appears to be higher among the patients with 11βHSD positive cells, the overall fertilization rates did not differ significantly between patients with 11βHSD positive and 11βHSD negative cells.

EXAMPLE 2

Granulosa cells were recovered from follicular aspirates of 16 women undergoing oocyte retrieval in 2 consecutive cycles. Following a 3 day preculture in serum-supplemented medium as described above in Example 1, cells were incubated for 4 hours in serum-free medium containing 100 nM [$^3$H]-cortisol and 11β-HSD activities were calculated as in Example 1. Of the 11 patients whose cells had detectable 11β-HSD activity in their initial treatment cycles, only 6 had 11β-HSD "positive" cells in their repeat cycles. Similarly, of the 5 patients studied with 11βHSD negative initial cycles, only 2 had 11β-HSD negative repeat cycles. Hence, there was no significant association between the presence or absence of detectable ovarian 11βHSD activity in consecutive IVF-ET cycles (Chi$^2$=0.042,n.s.). Furthermore, the clinical pregnancy rates were 0% and 67% for the 11βHSD positive and 11βHSD negative repeat cycles respectively. Thus, ovarian 11βHSD activity can vary for a given patient between IVF-ET cycles. This enzyme activity relates to the probability of conception by IVF-ET independently in initial and repeat treatment cycles.

We claim:

1. A method for predicting the outcome of in vitro fertilization-embryo transfer (IVF-ET) which comprises:
   (i) determining a level of 11β-hydroxysteroid dehydrogenase (11β-HSD) in a biological sample from a female subject; and
   (ii) predicting from the level of 11β-HSD determined the probability of establishing pregnancy in said subject by IVF-ET.

2. A method according to claim 1 wherein the sample is tissue from the environment of the oocyte.

3. A method according to claim 2 wherein the sample is a follicular aspirate.

4. A method according to claim 1 wherein the sample comprises granulosa lutein cells.

5. A method according to claim 1 wherein the level of 11β-HSD is determined by measuring the rate of conversion of cortisol to cortisone.

6. A method according to claim 1 wherein the female subject is a human female.

7. A method for predicting whether a fertilized oocyte will result in pregnancy in a female subject following IVF-ET which comprises:
   (i) removing a biological sample from the subject;
   (ii) determining a level of 11β-hydroxysteroid dehydrogenase (11β-HSD) in the sample; and
   (iii) predicting from the level of 11β-HSD the probability of establishing pregnancy in said subject by IVF-ET.

8. A method according to claim 7 wherein the female subject is a human female.

9. A method for predicting whether implantation of a fertilized oocyte will result in pregnancy in a female subject following IVF-ET which comprises:
   (i) removing oocytes from a female subject together with a biological sample;
   (i') fertilising said oocytes in vitro;
   (ii) determining the level of 11β-hydroxysteroid dehydrogenase (11β-HSD) in a sample; and
   (iii) predicting from the level of 11β-HSD determined the probability of establishing pregnancy in said subject by IVF-ET.

10. A method according to claim 9 which further comprises:
    (iv) implanting into the female subject the fertilized oocytes.

11. A method according to claim 9 wherein the sample comprises granulosa lutein cells.

12. A method for predicting whether implantation of a fertilized oocyte will result in pregnancy in a female subject following IVF-ET which comprises:
    (i) removing oocytes from a female subject together with a biological sample;
    (ii) determining a level of 11β-hydroxysteroid dehydrogenase (11β-HSD) in said sample;
    (iii) predicting from the level of 11β-HSD determined the probability of establishing pregnancy in said subject by IVF-ET; and
    (iii') fertilising oocytes from those patients whose 11β-HSD activity is below a predetermined threshold level.

13. A method according to claim 12 wherein the biological sample comprises granulosa lutein cells.

14. A method according to claim 12 wherein the predetermined threshold level is measured as the rate of conversion of $^3$H-cortisol to $^3$H-cortisone per mg protein per hour and is about 10 pmol/mg/4 hr.

15. A method according to claim 12 which further comprises:
    (iv) implanting into the female subject the fertilized oocytes.

16. A method of screening a female population for their suitability for IVF-ET which comprises:
    (i) screening a population of female subjects seeking treatment for infertility by IVF by determining levels of 11β-HSD in a biological sample from each patient; and
    (ii) selecting from the population of those patients who have 11β-HSD levels below a predetermined threshold for IVF-ET treatment.

17. A method according to claim 16 which further comprises re-screening patients with 11β-HSD levels above the predetermined threshold level for 11β-HSD levels in subsequent cycles of ovulation.

* * * * *